United States Patent [19]

Cordier

[11] 4,410,737

[45] Oct. 18, 1983

[54] PREPARATION OF META-CHLOROPHENOLS BY SELECTIVE HYDRODECHLORINATION OF POLYCHLOROPHENOLS

[75] Inventor: Georges Cordier, Francheville, France

[73] Assignee: Rhone-Poulenc Industries, Paris, France

[21] Appl. No.: 332,833

[22] Filed: Dec. 21, 1981

[30] Foreign Application Priority Data

Dec. 24, 1980 [FR] France ............................... 80 27936

[51] Int. Cl.³ .............................................. C07C 39/24
[52] U.S. Cl. .................................. 568/774; 568/716; 568/745; 568/746
[58] Field of Search ................ 568/774, 745, 746, 716

[56] References Cited

U.S. PATENT DOCUMENTS

| | | | |
|---|---|---|---|
| 2,803,669 | 8/1957 | Brainerd et al. | 568/774 |
| 3,912,782 | 10/1975 | Kiel et al. | 568/774 |
| 3,912,783 | 10/1975 | Wedemeyer et al. | 568/774 |
| 4,060,562 | 11/1977 | Wedemeyer et al. | 568/774 |

*Primary Examiner*—Werren B. Lone
*Attorney, Agent, or Firm*—Burns, Doane, Swecker & Mathis

[57] ABSTRACT

Meta-chlorophenols useful as intermediates in various organic syntheses are prepared by selectively catalytically hydrodechlorinating a polychlorophenol in liquid phase in an acid solvent medium which is at least partially aqueous and which comprises halide ions, in the presence of a Group VIII noble metal catalyst, said polychlorophenol bearing chlorine substituents in both the meta- and ortho- and/or para-positions.

26 Claims, No Drawings

PREPARATION OF META-CHLOROPHENOLS BY SELECTIVE HYDRODECHLORINATION OF POLYCHLOROPHENOLS

CROSS-REFERENCE TO RELATED APPLICATIONS

My copending applications, Ser. No. 332,846 and Ser. No. 332,740, both filed concurrently herewith; and both assigned to the assignee hereof.

BACKGROUND OF THE INVENTION

1. Field of the Invention

The present invention relates to the preparation of phenols containing a nuclear chlorine substituent in at least one of the meta-positions relative to the phenolic hydroxyl function, and, more especially, to the preparation of such meta-chlorophenols via the hydrodechlorination of the more highly chlorinated chlorophenols.

As utilized and intended herein, the expression "meta-chlorophenols" will hereafter connote phenols bearing a chlorine atom substituent in at least one of the meta-positions.

The meta-chlorophenols, and in particular 3-chlorophenol and 3,5-dichlorophenol, are compounds which are of very great industrial value as intermediates in various organic syntheses.

2. Description of the Prior Art

A plurality of methods for the preparation of the meta-chlorophenols have heretofore been proposed to this art. Methods for generating the phenol group in chlorine-substituted aromatic compounds (for example, by alkaline hydrolysis of polychlorobenzenes, or by nitration of 3-chlorobenzene and 3,5-dichlorobenzene, followed by the reduction of the nitro group to an amino group, the diazotization of the latter and ultimate decomposition of the diazonium salt), methods for chlorinating polychlorophenols are particularly exemplary. The latter method is of very great industrial value because of the availability of the polychlorophenols, certain of which are conventional compounds, while others are by-products of limited value, which it is important to utilize.

Thus, for example, isomeric trichlorophenols and tetrachlorophenols, some of which contain one or two chlorine atoms in the meta-position relative to the phenolic hydroxyl, are obtained during the preparation of 2,3,4,6-tetrachlorophenol and pentachlorophenol by chlorinating 2,6-dichlorophenol, which is a by-product from the preparation of 2,4-dichlorophenol. These various polychlorophenols constitute preferred starting materials for the preparation of meta-chlorophenols by dechlorination. One method for removing the excess chlorine atoms consists of subjecting the polychlorophenols to hydrogenation in the vapor phase or in the liquid phase, in the presence of a catalyst. For reasons of simplicity, the expression "hydrodechlorination" will hereafter connote the dechlorination of polychlorophenols by hydrogenation.

The crux of the problem presented by the hydrodechlorination of polychlorophenols to yield 3-chlorophenol or 3,5-dichlorophenol is the selective removal of the chlorine atoms in the 2- and/or 4- and/or 6-positions relative to the phenolic hydroxyl. Various processes for the hydrodechlorination of polychlorophenols have been proposed, but to date none has proved fully satisfactory.

Thus, U.S. Pat. No. 2,803,669 features a process for the hydrodechlorination of polychlorophenols in the vapor phase, by passing a gaseous mixture of hydrogen and polychlorophenols over a catalyst based on cuprous halides (for example, cuprous chloride) deposited on alumina, the catalyst being maintained at highly elevated temperature (350° to 550° C.). When applied to the hydrodechlorination of 2,3,4,6-tetrachlorophenol, this process does not permit of the selective removal of the chlorine atoms in the 2-, 4- and 6-positions relative to the phenolic hydroxyl function. Indeed, the reaction mixture resulting from the hydrogenation essentially consists of 2,4-dichlorophenol and 2,6-dichlorophenol.

And French patent application No. 73/43,484, published under No. 2,209,738, proposes a process for the preparation of meta-halogenophenols by dehalogenating polyhalogenophenols by hydrogenation in the liquid phase at an elevated temperature, in the presence of a catalyst comprising either one or more sulfides or polysulfides of iron, nickel or cobalt, or a noble metal, such as palladium or platinum, associated with a sulfur derivative. The reaction is preferably carried out in the presence of a base, such as alkali metal hydroxides or carbonates, in order to neutralize the hydracids generated by the reaction, as they are formed. Although this process is shown to be very selective with respect to the formation of meta-chlorophenols, it displays the distinct disadvantage in that it must be carried out in the presence of a base, and in particular an alkali metal base, under temperatures (the temperature must preferably be between 180° and 330° C.) which favor the formation of halogenodioxins, and in particular of polychlorodioxins, certain of which are known to be highly toxic. In practice, a disadvantage of this type renders the process devoid of any meaningful industrial value. Thus, serious need exists in this art for a selective process for obtaining meta-chlorophenols via the hydrodechlorination of polychlorophenols, which process would obviate the need for the presence of alkali metal bases.

SUMMARY OF THE INVENTION

Accordingly, a major object of the present invention is the provision of an improved process for the selective hydrodechlorination of polychlorophenols, which improved process is conspicuously devoid of those disadvantages and drawbacks immediately above outlined.

Briefly, the present invention features a process for selectively preparing chlorophenols bearing a chlorine atom substituent in at least one of the meta-positions relative to the phenolic hydroxyl group, by the hydrogenation, under the influence of heat, in the liquid phase, and in the presence of a catalyst based on a noble metal of Group VIII of the Periodic Table, of polychlorophenols having the structural formula (I):

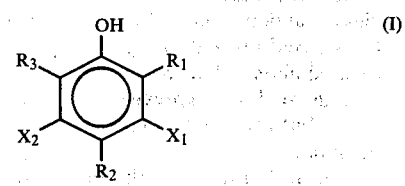

in which: $X_1$ and $X_2$, which are identical or different, each represents a chlorine atom, a hydrogen atom or an alkyl, aryl, arylalkyl, alkoxy or aryloxy radical, at least one of the symbols $X_1$ and $X_2$ representing a chlorine atom, and $R_1$, $R_2$ and $R_3$, which may also be identical or different, each represents a chlorine atom, a hydrogen atom, an alkyl radical, an aryl or arylalkyl radical or an alkoxy or aryloxy radical, at least one of the symbols $R_1$, $R_2$ and $R_3$ representing a chlorine atom, and said hydrodechlorination being characterized in that it is carried out in an acid solvent medium which is at least partially aqueous and which contains halide ions.

DETAILED DESCRIPTION OF THE INVENTION

More particularly according to this invention, in the formula (I), those radicals $X_1$, $X_2$, $R_1$ and $R_3$ which do not symbolize a chlorine atom represent more advantageously an alkyl radical containing from 1 to 10 carbon atoms and preferably from 1 to 4 carbon atoms, such as methyl, ethyl, n-propyl, isopropyl, n-butyl, isobutyl or t-butyl radicals, a phenyl radical, a benzyl radical, an alkoxy radical containing from 1 to 10 and preferably from 1 to 4 carbon atoms, such as methoxy, ethoxy, n-propoxy, isopropoxy or n-butoxy radicals, or the phenoxy radical.

Among the halide ions which are suitable for carrying out the process according to the invention, representative are the chloride, bromide and iodide ions, which can either be individually used, or used in any combination thereof. It is preferred to individually use bromide and chloride ions, or the combinations $Cl^-/I^-$ and $Cl^-/Br^-$.

The solvent medium in which the reaction is carried out can exclusively consist of water, or of a mixture, in all proportions, of water and one or more organic solvents which are liquid and inert under the conditions of reaction. It is not necessary for this solvent or these solvents to be miscible with water; their function consists essentially in dissolving the polychlorophenols. Examples of solvents which are representative are: aliphatic hydrocarbons such as octane and hexane, cycloaliphatic hydrocarbons such as cyclohexane, aromatic hydrocarbons such as benzene, toluene and xylenes, and aromatic chlorohydrocarbons such as mono-chlorobenzene and polychlorobenzenes.

Among these solvents, monochlorobenzene and the polychlorobenzenes are of particular value.

Essentially because of their boiling points, it is more preferable to use dichlorobenzenes and trichlorobenzenes if the solvent medium for the reaction consists of a mixture of water and organic solvent.

The volume ratio water/organic solvent is not critical; the water can represent, for example, from 5% to 100% of the total volume of the solvent medium. Most advantageously, the water constitutes from 50 to 100% of the total volume of the solvent medium.

For convenience, the term "aqueous solution" will hereafter be used to connote the solvent medium in which the reaction is carried out, but it should be clearly understood that this term also includes the solutions based on water/organic solvent mixtures such as defined above. The concentrations of the various compounds will be expressed, not relative to the water alone, but relative to the overall volume of the solvent medium.

The acid aqueous solutions containing halide ions, used as the reaction medium for carrying out the process according to the invention, can be obtained by adding one or more compounds releasing halide ions in aqueous solution, which compounds shall be hereafter referred to as "halide carriers" for convenience, to aqueous solutions of strong non-halogenated mineral acids such as sulfuric acid or phosphoric acid. Among these halide carriers, representative are the alkali metal or alkaline earth metal halides (chlorides, bromides and iodides), ammonium halides, quaternary ammonium halides and amine hydrohalides. More simply, it is preferred to use aqueous solutions of hydrochloric acid, hydrobromic acid and hydriodic acid, which provide the reaction medium with both the acidity and the chloride, bromide and iodide ions necessary for carrying out the hydrodechlorination.

The acidity of the medium can vary over wide limits. Preferably, the concentrations of protons in the aqueous solution is at least 0.5 $H^+$ ion per liter. There is no critical upper limit for this concentration, although excessive acidity of the reaction medium is not desirable, such that corrosion of the apparatus will be curtailed. Typically, the concentration of protons does not exceed 15 $H^+$ ions per liter, and, if the nature of the acid employed so permits, does not exceed 8 $H^+$ ions per liter. In practice, the concentration of protons preferably ranges from 1 to 6 $H^+$ ions per liter.

As a general proposition, there is no critical maximum limit on the concentration of halide ions; however, for practical reasons, it is not necessary to exceed a concentration of 15 g ions/liter of halide. On the other hand, it too has been found that the concentration of halide ions in the aqueous phase cannot be reduced below a minimum value if it is desired to preserve the selective nature of the hydrodechlorination. This critical minimum value depends upon the nature of the halide. Thus, if the halide ion is the bromide ion, the concentration of $Br^-$ can be reduced to 2 g ions/liter and preferably to 4 g ions/liter, while at the same time preserving an excellent selectivity of hydrodechlorination. In the case of chloride ions, the concentration is preferably equal to at least 8 $Cl^-$ ions per liter and even more preferably equal to at least 10 $Cl^-$ ions per liter. In this case, it is found that if hydrochloric acid is used to provide protons and chloride ions, the concentration of protons is dependent upon the minimum concentration of chloride ions. The use of high concentrations of chloride ions results, ipso facto, in a higher concentration of protons than is strictly necessary for carrying out the reaction satisfactorily. Under these conditions, the use of hydrochloric acid, which is more advantageous than that of hydrobromic acid from an economic point of view, has a considerable disadvantage from the point of view of corrosion. It is of course notably advantageous from an industrial point of view to limit the acidity of the medium such as to curtail as much corrosion as is possible. It has been found that hydrochloric acid can be used at concentrations of less than 8 mols per liter and, in particular, at concentrations which impart to the medium an acidity falling within those limits outlined hereinabove, without thereby adversely affecting the satisfactory course of the reaction, provided that compounds which provide the reaction medium with halide ions without modification, or with only slight modification, of the acidity of this medium are used conjointly; and this finding circumscribes yet another embodiment of the present invention.

Among the compounds which are suitable in this respect and which will hereafter be referred to as "halide carriers," exemplary are the alkali metal or alkaline earth metal halides, such as the chlorides, bromides and iodides of sodium, potassium and lithium, ammonium chloride, iodide and bromide, quaternary ammonium chlorides, iodides and bromides, such as tetraethylammonium chloride, iodide and bromide, and amine hydrohalides. It is also possible to use hydrobromic acid and hydriodic acid, which can be used in a small amount and which do not substantially modify or adjust the acidity of the medium. It is preferred to use alkali metal halides, and it is even more preferred to use alkali metal bromides and iodides.

The amount of halide carrier used conjointly with the hydrochloric acid depends essentially upon the nature of the halide ion. Thus, if a chloride is used, this amount is calculated such that the total concentration of chloride ions in the acid aqueous solution is equal to at least 8 chloride ions per liter. The expression "total concentration of chloride ions" is to be understood as intending the concentration of chloride ions originating from the hydrochloric acid, on the one hand, and from the chloride ion carrier used, on the other hand. In such a case, the amount of hydrochloric acid is calculated such that the concentration of protons is within the limits indicated above and in particular ranges from 1 to 6 H$^+$ ions per liter, the remaining chloride ions necessary to reach the minimum value of the concentration of Cl$^-$ ions being provided by the chloride ion carrier employed. If iodide carriers or bromide ion carriers are used, it will be possible for the amounts used to be substantially less than those of the chloride ion carriers. In fact, it has been found that concentrations of I$^-$ ions as low as $1.10^{-6}$ I$^-$ ion per liter, and concentrations of Br$^-$ ions as low as $1.10^{-2}$ Br$^-$ ion per liter, enable the obtainment of good results. Preferably, the concentration of I$^-$ ions in the reaction medium is equal to at least $1.10^{-4}$ I$^-$ ion per liter and the concentration of bromide ions is equal to at least 0.1 Br$^-$ ion per liter. There is no critical upper limit to the concentrations of halide ions, as above indicated. Nevertheless, for practical reasons, it is not necessary to exceed 1 I$^-$ ion per liter and 10 Br$^-$ ions per liter, and preferably not to exceed 6 Br$^-$ ions per liter.

It is also possible, without departing from the scope of the present invention, to use hydrochloric acid conjointly with two or more halide ion carriers, but this would not provide any particular advantage.

The noble metals upon which the catalysts utilized per the invention are based, are mainly metals of Group VIII of the Periodic Table, such as ruthenium, rhodium, palladium, osmium, iridium and platinum. Palladium is the preferred metal. The metal can be in the pure metallic state or in the form of chemical compounds thereof; in general, the metal is preferably used in the metallic form because, under the operating conditions of reaction, compounds tend to be reduced to their metallic state. The catalyst can either be supported or unsupported. Any inert support which is itself known can be used as the catalyst support; more particularly suitable supports which are exemplary are carbon black, silica and barium sulfate; carbon black is a preferred support. The catalyst and its support are advantageously in a finely divided form; specific surface areas of more than 100 m$^2$/g are generally suitable.

The amount of catalyst used is such that the proportion by weight of noble metal of the catalyst, relative to the compound of the formula (I) to be treated, typically ranges from 0.01 to 10% and preferably from 0.1 to 5%.

The reaction temperature typically ranges from 50° to 350° C. and preferably from 100° to 250° C.

The hydrogen partial pressure can also vary over wide limits and be greater than, less than or equal to atmospheric pressure. More specifically, the hydrogen pressure ranges from 0.1 to 60 bars and preferably from 0.5 to 50 bars. Pressures of more than 60 bars could indeed be used, but this does not result in any particular advantages. The total pressure at which the reaction is carried out essentially depends on the temperature conditions, the volatility, under these conditions, of the acid used and the degree of the hydrogen partial pressure. It is self-evident that the total pressure must be sufficient to maintain the reaction medium liquid and/or to maintain the concentration of acid in the aqueous phase within the aforenoted limits.

Exemplary of the polychlorophenols of the formula (I) which are useful starting materials in the process according to the present invention are: 2,3-dichlorophenol, 2,5-dichlorophenol, 3,4-dichlorophenol, 2,3,4-trichlorophenol, 2,3,6-trichlorophenol, 2,4,5-trichlorophenol, 2,3,5-trichlorophenol, 3,4,5-trichlorophenol, 2,3,4,6-tetrachlorophenol, 2,3,4,5-tetrachlorophenol, 2,3,5,6-tetrachlorophenol, pentachlorophenol, 2,3,4-trichloro-6-methylphenol, 2,3-dichloro-6-methylphenol, 2,3,4,6-tetrachloro-5-methylphenol, 2,3-dichloro-4-methylphenol, 2,3,5,6-tetrachloro-4-methylphenol, 2,5-dichloro-3,4-dimethylphenol, 2,5-dichloro-4-ethylphenol, 2,5-dichloro-4-propylphenol, 2,5-dichloro-4-t-butylphenol, 3,4,6-trichloro-2-benzylphenol, 3,4-dichloro-2-methoxyphenol, 3,6-dichloro-2-methoxyphenol, 4,5-dichloro-2-methoxyphenol, 5,6-dichloro-2-methoxyphenol, 3,4,6-trichloro-2-methoxyphenol, 3,4,5-trichloro-2-methoxyphenol, 3,4,5,6-tetrachloro-2-methoxyphenol, 4,5-dichloro-3-methoxyphenol, 5,6-dichloro-3-methoxyphenol, 2,5-dichloro-3-methoxyphenol, 4,5,6-trichloro-3-methoxyphenol, 2,3,6-trichloro-3-methoxyphenol, 4,5-dichloro-2-phenoxyphenol, 2,3,5,6-tetrachloro-4-phenoxyphenol, 3,4-dichloro-3-ethoxyphenol, 3,4,5-trichloro-2-ethoxyphenol, 3,4-dichloro-2-phenylphenol and 3,5,6-trichloro-2-phenylphenol.

In actual practice, the dichlorophenols and trichlorophenols are preferably used.

The following are exemplary of those phenols bearing a chlorine atom substituent in at least one of the meta-positions relative to the phenolic hydroxyl group, which are conveniently prepared by the process according to the present invention: 3-chlorophenol, 3,5-dichlorophenol, 3-chloro-6-methylphenol, 3-chloro-5-methylphenol, 3-chloro-4-methylphenol, 3,5-dichloro-4-methylphenol, 5-chloro-3,4-dimethylphenol, 3,5-dichloro-4-ethylphenol, 3,5-dichloro-4-propylphenol, 3,5-dichloro-4-t-butylphenol, 3-chloro-2-benzylphenol, 3-chloro-2-methoxyphenol, 3-chloro-6-methoxyphenol, 3,5-dichloro-2-methoxyphenol, 3-chloro-5-methoxyphenol, 3-chloro-6-phenoxyphenol, 3,5-dichloro-6-phenoxyphenol, 3-chloro-2-ethoxyphenol and 3-chloro-2-phenylphenol.

The process according to the invention can be carried out either continuously or batchwise. Upon completion of the reaction, the catalyst is filtered off and can be recycled as such into a further hydrodechlorination operation. The meta-chlorophenols formed can easily be separated from the reaction mixture by extraction with an organic solvent which is immiscible with water, and then recovered by distillation, after removal of the solvent of extraction.

In order to further illustrate the present invention and the advantages thereof, the following specific examples are given, it being understood that same are intended only as illustrative and in nowise limitative.

EXAMPLE 1

The following materials were introduced into a 250 ml tantalum-lined stainless steel autoclave equipped with a stirring system:
 (i) 1 g of 3,4-dichlorophenol;
 (ii) 100 ml of a 12 N aqueous solution of hydrochloric acid; and
 (iii) 0.14 g of a catalyst consisting of palladium deposited on an active charcoal having a specific surface area of 1,000 $m^2.g^{-1}$, and containing 5% by weight of palladium metal (namely, 0.007 g of palladium).

After the autoclave had been closed, its contents were heated to 190° C., hydrogen was then introduced until the total pressure was 65 bars, and these conditions were maintained for 5 hours. The contents of the autoclave were subsequently cooled, degassed and then drawn off. The catalyst was separated from the aqueous phase. The chlorophenols were then extracted from the aqueous phase with 300 ml of ether. The catalyst was washed 3 times with 20 ml of ether in order to extract the chlorophenols which it contained. The ether extracts were combined, the ether was then removed by distillation and the chlorophenols present in the distillation residue were determined and identified by vapor phase chromatography.

The results of the analysis reflected that all of the 3,4-dichlorophenol had been converted [degree of conversion (DC): 100%]. The following were identified in the distillation residue:
 3-chlorophenol: yield relative to the 3,4-dichlorophenol introduced (RY)=93.3%
 phenol: RY=6.7%.

EXAMPLE 2

The procedure of Example 1 was repeated, but with the hydrochloric acid being replaced by a 6 N solution of hydrobromic acid, and hydrogen being introduced until a total pressure of 25 bars was obtained for a temperature of 190° C. These conditions were maintained for 90 minutes.

By thus operating, 3-chlorophenol was obtained with a yield of 100%, relative to the 3,4-dichlorophenol introduced (DC=100%).

EXAMPLE 3

The procedure of Example 1 was repeated, but with the 12 N aqueous solution of hydrochloric acid being replaced by 100 ml of a 6 N aqueous solution of HCl, and 0.022 g of potassium iodide (namely, 0.0013 mol per liter of solution) also being introduced.

The reaction time was 260 minutes. After separation and determination of the reaction products, it was found that the degree of conversion of the dichlorophenol was 100%, the RY of 3-chlorophenol was 95% and the RY of phenol was 5%.

By way of comparison, the previous experiment was repeated without introducing the potassium iodide, but with all other parameters being the same. Under these conditions, it was found that no 3-chlorophenol was formed, but that mainly cyclohexanol and cyclohexanone were formed.

EXAMPLE 4

The procedure of Example 3 was repeated, but with the 3,4-dichlorophenol being replaced by 2,5-dichlorophenol, and 0.11 g of potassium iodide was introduced per liter of aqueous solution of hydrochloric acid.

Under these conditions, the DC of the dichlorophenol was 93% and the yield of 3-chlorophenol, relative to the dichlorophenol converted (Y), was 100%.

EXAMPLE 5

The following materials were introduced into a 250 ml tantalum-lined stainless steel autoclave equipped with a stirring system:
 (i) 2.6 g of pentachlorophenol;
 (ii) 0.5 g of Pd-on-charcoal catalyst containing 5% of metal (identical to that of Example 1);
 (iii) 15 ml of 1,2-dichlorobenzene;
 (iv) 90 ml of 12 N aqueous hydrochloric acid;
 (v) 1.2 ml of 8 N aqueous hydriodic acid; and
 (vi) 30 ml of water.

The autoclave was closed and purged three times of the air which it contained with 5 bars of nitrogen and then purged three times with 5 bars of hydrogen. The autoclave was then pressurized with 20 bars of hydrogen (at ambient temperature). The contents were heated to 210° C. and the reaction was permitted to proceed at this temperature for 21 hours, 30 minutes. After cooling and degassing, the reaction mixture was treated as in Example 1.

The following results were obtained:
 DC of the pentachlorophenol: 100%
 RY of 3,5-dichlorophenol: 85%
 RY of 2,3,5-trichlorophenol: 5.1%
 RY of 2,3,5,6-tetrachlorophenol: 9.4%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the selective preparation of a meta-chlorophenol, comprising selectively catalytically hydrodechlorinating, with hydrogen, a polychlorophenol having the structural formula (I):

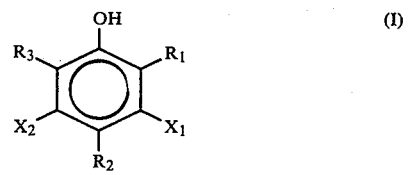

wherein $X_1$ and $X_2$, which may be identical or different, each represents a chlorine atom, a hydrogen atom or an alkyl, aryl, arylalkyl, alkoxy or aryloxy radical, at least one of $X_1$ or $X_2$ being a chlorine atom, and $R_1$, $R_2$ and $R_3$, which may also be identical or different, each represents a chlorine atom, a hydrogen atom, an alkyl, aryl, arylalkyl, alkoxy or aryloxy radical, at least one of $R_1$, $R_2$ or $R_3$ being a chlorine atom, and said selective catalytic hydrodechlorination being carried out at elevated temperatures in liquid phase in an acid solvent medium which is at least partially aqueous and which comprises halide ions, in the presence of a Group VIII noble metal catalyst.

2. The process as defined by claim 1, wherein said at least partially aqueous acid solvent medium comprises a water/organic solvent mixture containing from 5 to 100% by volume of water.

3. The process as defined by claim 2, said water/organic solvent mixture containing from 50 to 100% by volume of water.

4. The process as defined by claims 1, 2 or 3, wherein said polychlorophenol having the structural formula (I) those radicals $X_1$, $X_2$, $R_1$ and $R_3$ which are not a chlorine atom represent an alkyl radical containing from 1 to 10 carbon toms, a phenyl radical, a benzyl radical, an alkoxy radical containing from 1 to B 10 carbon atoms or a phenoxy radical.

5. The process as defined by claims 1, 2 or 3, wherein the concentration of protons in said aqueous acid solvent medium is at least 0.5 g ion/liter.

6. The process as defined by claim 5, wherein the concentration of protons in said aqueous acid solvent medium is at most 15 g ions/liter.

7. The process as defined by claim 6, wherein the concentration of halide ions in said aqueous acid solvent medium is at least 2 g ions/liter.

8. The process as defined by claim 7, wherein the concentration of halide ions in said aqueous acid solvent medium is at most 15 g ions/liter.

9. The process as defined by claim 8, wherein said aqueous acid solvent medium comprising halide ions is an aqueous solution of hydrochloric acid, hydrobromic acid or hydriodic acid.

10. The process as defined by claim 8, wherein said aqueous acid solvent medium comprising halide ions comprises chloride ions in combination with bromide and/or iodide ions.

11. The process as defined by claim 8, wherein said aqueous acid solvent medium comprising halide ions is an aqueous solution of hydrochloric acid and of at least one chloride, bromide or iodide ion carrier.

12. The process as defined by claim 1, wherein said halide ion carrier is hydrobromic acid, hydriodic acid, alkali metal and alkaline earth metal chlorides, bromides and iodides, ammonium and quaternary ammonium chlorides, bromides and iodides or amine hydrochlorides, hydrobromides and hydriodides.

13. The process as defined by claim 12, wherein the carrier is a chloride ion carrier, in an amount such that the total concentration of chloride ions in the aqueous acid solvent medium is at least 8 g ions/liter.

14. The process as defined by claim 12, wherein the halide ion carrier is an iodide or bromide ion carrier, and the concentration of the aqueous solution of hydrochloric acid is at least 0.5 mol/liter.

15. The process as defined by claim 14, wherein the carrier is an iodide ion carrier, in an amount such that the concentration of iodide ions in the aqueous solution of hydrochloric acid ranges from $1.10^{-6}$ to 1 $I^-$ ion per liter.

16. The process as defined by claim 14, wherein the carrier is a bromide ion carrier, in an amount such that the concentration of bromide ions in the aqueous solution of hydrochloric acid ranges from $1.10^{-2}$ to 10 $Br^-$ ions per liter.

17. The process as defined by claim 12, wherein the halide ion carrier is a chloride, bromide or iodide of sodium or potassium.

18. The process as defined by claim 17, wherein the hydrodechlorination reaction temperature ranges from 50° to 350° C.

19. The process as defined by claim 18, wherein the hydrogen partial pressure ranges from 0.1 to 60 bars.

20. The process as defined by claim 20, wherein said catalyst is palladium deposited on an inert support.

21. The process as defined by claim 19, wherein the amount of catalyst, expressed as the weight of noble metal per 100 g of polychlorophenol having the structural formula (I), ranges from 0.01 g to 10 g.

22. The process as defined by claim 19, wherein the polychlorophenol having the structural formula (I) is a dichlorophenol or trichlorophenol bearing a chlorine atom substituent in at least one of the meta-positions relative to the phenolic hydroxyl group.

23. The process as defined by claim 22, wherein the polychlorophenol having the structural formula (I) is 3,4-dichlorophenol, 2,5-dichlorophenol or pentachlorophenol.

24. The process as defined by claims 1, 2 or 3, wherein said polychlorophenol having the structural formula (I) is 2,3-dichlorophenol, 2,5-dichlorophenol, 3,4-dichlorophenol, 2,3,4-trichlorophenol, 2,3,6-trichlorophenol, 2,4,5-trichlorophenol, 2,3,5-trichlorophenol, 3,4,5-trichlorophenol, 2,3,4,6-tetrachlorophenol, 2,3,4,5-tetrachlorophenol, 2,3,5,6-tetrachlorophenol, pentachlorophenol, 2,3,4-trichloro-6-methylphenol, 2,3-dichloro-6-methylphenol, 2,3,4,6-tetrachloro-5-methylphenol, 2,3-dichloro-4-methylphenol, 2,3,5,6-tetrachloro-4-methylphenol, 2,5-dichloro-3,4-dimethylphenol, 2,5-dichloro-4-ethylphenol, 2,5-dichloro-4-propylphenol, 2,5-dichloro-4-t-butylphenol, 3,4,6-trichloro-2-benzylphenol, 3,4-dichloro-2-methoxyphenol, 3,6-dichloro-2-methoxyphenol, 4,5-dichloro-2-methoxyphenol, 5,6-dichloro-2-methoxyphenol, 3,4,6-trichloro-2-methoxyphenol, 3,4,5-trichloro-2-methoxyphenol, 3,4,5,6-tetrachloro-2-methoxyphenol, 4,5-dichloro-3-methoxyphenol, 5,6-dichloro-3-methoxyphenol, 2,5-dichloro-3-methoxyphenol, 4,5,6-trichloro-3-methoxyphenol, 2,3,6-trichloro-3-methoxyphenol, 4,5-dichloro-2-phenoxyphenol, 2,3,5,6-tetrachloro-4-phenoxyphenol, 3,4-dichloro-3-ethoxyphenol, 3,4,5-trichloro-2-ethoxyphenol, 3,4-dichloro-2-phenylphenol or 3,5,6-trichloro-2-phenylphenol.

25. The process of claim 1, wherein the Group VIII metal catalyst is in a metallic state.

26. The process of claim 1, wherein the hydrodechlorination reaction temperature ranges from 50° to 350° C., and the hydrogen partial pressure ranges from 0.1 to 60 bars.

* * * * *